United States Patent [19]

Tang et al.

[11] Patent Number: 5,077,388
[45] Date of Patent: Dec. 31, 1991

[54] PURIFICATION OF HUMAN INTERLEUKIN-4 FROM A SECRETED ESCHERICHIA COLI MUTANT

[75] Inventors: John C. T. Tang, Livingston, N.J.; David Naveh, AG Leiden, Netherlands; Tattanahali L. Nagabhushan, Parsippany, N.J.

[73] Assignee: Schering Corporation, Kenilworth, N.J.

[21] Appl. No.: 531,270

[22] Filed: May 31, 1990

[51] Int. Cl.$^5$ ............................................... C07K 3/28
[52] U.S. Cl. .................................. 530/351; 424/85.2; 435/69.52
[58] Field of Search ...................... 530/351; 435/69.52

[56] References Cited

PUBLICATIONS

Dwyer, Biotechnology, 2, 957 (1984).
Yokota, et al., Proc. Natl. Acad. Sci. U.S.A. 83, 5894-5898 (1986).
Lee et al., Proc. Natl. Acad, Sci., U.S.A., 83, 2061-2065 (1986).
Noma, et al., Nature 319, 640-646 (1986).

*Primary Examiner*—Howard E. Schain
*Assistant Examiner*—P. Lynn Touzeau
*Attorney, Agent, or Firm*—James R. Nelson; Gerald S. Rosen; Norman C. Dulak

[57] ABSTRACT

Active recombinant human IL-4 is purified from a crude fermentation broth of a secreted *E. coli* mutant by subjecting said solution to selective chromatogrphy on a zinc-chelating agarose column at pH 7.2 in a buffer containing a high concentration of sodium chloride, i.e., about 1M sodium chloride, washing first with a phosphate buffer at pH 7.2 containing 1.0M sodium chloride then with a buffer containing 10% glycerol and eluting at pH 5.0. The resulting purified active recombinant human IL-4 solution is further treated by cation exchange chromatography, concentration by diafiltration up to 20 mg/mL and size exclusion gel chromatography using a citrate buffer at pH 4.5.

11 Claims, No Drawings

PURIFICATION OF HUMAN INTERLEUKIN-4 FROM A SECRETED ESCHERICHIA COLI MUTANT

FIELD OF INVENTION

This invention relates generally to a method for extracting and purifying proteins from bacteria, and more particularly to methods for extracting and purifying soluble active human interleukin-4 expressed in *Escherichia Coli* (*E. Coli*).

BACKGROUND

Human interleukin-4 (IL-4) is a natural protein which is believed to have a therapeutic potential against infection, cancer and autoimmune disease and was characterized by Yokota et al., Proc. Natl. Acad. Sci.,USA, 83, 5894-5898 (1986). Mouse IL-4 is reported by Lee, et al., Proc. Natl. Acad. Sci. USA, 83, 2061-2065 (1986) and Noma, et al. Nature, 319, 640-646 (1986).

In the production of genetically engineered IL-4, separation of the expressed protein from the transformed host cells or their cultures supernatants can be a major problem, Dwyer, Biotechnology, 2, 957 (1984).

E. coli expression of IL-4 in *E. coli* can be intracellular insoluble aggregates (inclusion bodies) or active soluble material secreted into the periplasmic space or culture medium (fermentation broth). This invention relates to extracting and purifying active soluble IL-4 resulting from its expression in certain strains of *E. coli*.

Clinical use of active IL-4 requires a high purity material that is not contaminated by cell constituents or cell debris of the IL-4 expressing cell. Accordingly, purification of active IL-4 in the fermentation broth of IL-4 expressing *E. coli* in high yields and high purity is needed.

SUMMARY OF THE INVENTION

The present invention is based on the discovery that high purity active IL-4 can be obtained from the fermentation broth of IL-4 expressing *E. coli* in a three-step process comprising:

1. Subjecting crude fermentation broth to affinity chromatography on a metal chelating-agarose gel column such as a chelating-Sepharose ® gel available from Pharmacia Fine Chemicals, Piscataway, N.J. under the names chelating-Sepharose ® Fast Flow and chelating-Sepharose ® 6B. Chelating Sepharose ® Fast Flow consists of iminodiacetic acid groups on spacers coupled to Sepharose 6 Fast Flow by stable ether linkages. Sepharose ® 6 Fast Flow is a cross-linked agarose, 6%. A buffer, preferably a phosphate buffer, is used. The phosphate buffer used is one with a high sodium chloride concentration, i.e. about 0.5 to 1.5M, preferably 1.0M, in a neutral to slightly alkaline pH, i.e. about pH 6.7-8, preferably about 7.2. The high salt concentration and near neutral pH of about 7.2 helps maximize binding of the active interleukin-4 and minimize binding of other proteins to the column. The preferred metal chelate is zinc, although other metal chelates such as copper, cobalt or nickel can be used. After the binding is completed, the column is washed twice, first with an equilibration buffer containing 20 mM sodium phosphate, pH 7.2 and 1.0M sodium chloride. It is then washed with the phosphate buffer containing about 10% glycerol and a low concentration of sodium chloride, i.e. about 150 mM, in a 20 mM sodium phosphate buffer. The second washing removes impurities including very closely related hard to separate impurities. Finally, the active IL-4 is eluted at pH 5.0 with an acetate buffer containing 0.50M sodium chloride.

2. Subjecting the solution of active IL-4 from step 1 to cation exchange chromatography on a S-Sepharose ® Fast Flow column at a near neutral pH of about 6.75 and at 15 mS(conductivity) where most impurities do not bind. The further purified IL-4 in a buffered solution is then eluted from the column; and 3. Subjecting the active IL-4 solution to gel filtration chromatography on a size exclusion column equilibrated with 10 mM sodium citrate, pH 4.5 after concentration up to 20 mg/ml at pH 4.5. Then collecting the purified active IL-4 solution which is 95%-99% pure.

DETAILED DESCRIPTION

The method of this invention makes it possible to subject a crude solution of active recombinant human interleukin 4 to affinity chromatography, cation exchange chromatography and size exclusion chromatography to obtain high purity active IL-4. By using a buffer at near neutral, preferably pH 7.2, and high concentrations of sodium chloride, preferably 1 M sodium chloride, active IL-4 molecules are selectively bound by affinity chromatography to a metal chelatingagarose gel column, preferably chelating Sepharose Fast Flow or Sepharose 6B, to the substantial exclusion of contaminating proteins present in the solution.

The source of the crude solution of active IL-4 is not critical to the process of this invention. Preferred sources are the fermentation broths containing dissolved or secreted therein active human IL-4. Preferably, the active human IL-4 is expressed into the broth by certain strains of E. coli.

Thus the invention is a process for purifying a crude solution of active recombinant human IL-4 comprising (a) subjecting a buffered crude solution of said IL-4 at a neutral to a slightly alkaline pH and containing about 0.5 to 1.5 molar sodium chloride to affinity chromatography on a metal chelating-agarose gel to selectively bind the IL-4;

(b) washing the column first with a 20 mM sodium phosphate equilibration buffer at pH 7.2 containing 1.0M sodium chloride, then with the buffer containing 10% glycerol by volume and about 150 mM of sodium chloride;

(c) eluting the bound IL-4 with an eluting buffer at an acid pH or a neutral pH buffer containing a chelating agent, an analog of histidine or an amino acid;

(d) treating the active IL-4 eluate from step (c) with a cation exchange chromatography column such as S-Sepharose ® (available from Pharmacia Fine Chemicals) at a near neutral to slightly acid pH and at a conductivity of 15 mS, S-Sepharose ® is a cross-linked agarose matrix having coupled thereto the ion exchange group —$CH_2$— $SO_3$— $Na^+$;

(e) concentrating the eluate from step (d) with an ultrafiltration membrane (10,000 molecular weight cutoff);

(f) treating the concentrated retentate by gel filtration chromatography on a size exclusion column; and (g) collecting the purified active IL-4.

The process of this invention in the most preferred embodiment comprises the following steps:

(a) charging a crude solution of active recombinant human IL-4 to an affinity chromatography column of a metal chelating-agarose gel, preferably chelating Sepharose ® Fast Flow, in a neutral to slightly alkaline pH phosphate buffer containing 1.0M sodium chloride;

(b) washing the column twice, first with a phosphate buffer at pH 7.2–7.5 containing 1.0M sodium chloride, then with the phosphate buffer containing 10% by volume of glycerol and 150 mM sodium chloride;

(c) isocratically eluting the active IL-4 from the column with an eluting acetate buffer at pH 5.0 containing 0.5M sodium chloride;

(d) subjecting the active IL-4 eluate in a phosphate buffer at pH 6.75, conductivity 15 mS, from step (c) to cation exchange chromatography on a column such as S-Sepharose ® equilibrated with 20 mM sodium phosphate buffer, pH 6.75 and 0.12M sodium chloride; and gradient eluting with a phosphate buffer at pH 6.75 having 0.12–0.6M NaCl;

(e) concentrating the eluate from step (d) with an ultrafiltration membrane;

(f) treating the concentrated eluate by gel filtration chromatography on a size exclusion column eqilibrated with 10 mM sodium citrate buffer at pH 4.5; and (g) collecting the purified active IL-4 solution.

In step (a) the crude solution charged to the metal chelating agarose column can be from any source, however, in the practice of this invention, it is preferred to utilize the fermentation broths that had previously been treated to remove cell debris and other large particles which result from fermentation processes. More particularly, the process of this invention is applicable to purification of active human IL-4 which is produced by E. coli strains which are genetically engineered to produce active human IL-4 and secrete the active human IL-4 into the culture medium (fermentation broth). The term "active human IL-4" as used herein means undenatured recombinant human IL-4 which is in its biologically active natural conformation.

Such genetic engineering usually entails the introduction of an expression vector into a bacterium. The expression vector is capable of autonomous replication and protein expression relative to genes in the bacterial genome. Construction of bacterial vectors is well known in the art, provided the nucleotide sequence encoding a desired protein is known or otherwise available.

Preferably the IL-4 is produced by a secretory E. coli strain as described in applicants assignees' U.S. patent application Ser. No. 07/429,588, filed Oct. 31, 1989, which application is incorporated in its entirety by reference herein. Of particular relevance are the Examples on pages 25–33, the data on pages 34–36, the recitation of the culture deposits on page 36 and the drawings.

The preferred E. coli strains used to prepare the active IL-4 purified according to this invention are RL 2117/pRGT857-11 and RL732I/pRGT857-11.

The preferred metal chelating-agarose utilized in step (a) is chelating Sepharose ® Fast Flow although chelating Sepharose ® 6B is also satisfactory. The Sepharoses are products of Pharmacia Fine Chemicals, Piscataway, N.J. A preferred method of preparing the preferred zinc chelating Sepharose ® column for use in this invention is by pouring the Sepharose ® gel into a chromatography column, washing with deionized water, then pumping a salt, preferably zinc acetate, solution and deionized water through the column, then pumping an equilibration buffer, i.e. 20 mM sodium phosphate, pH 7.2, 1.0M NaCl solution through the column. Instead of zinc acetate, other zinc salts may be used, e.g. zinc chloride or zinc sulfate.

The chromatography column is two columns connected in series. The first or top column contains the zinc chelating-Sepharose ® gel and the second or bottom column contains chelating Sepharose ® gel which has not been treated with a zinc salt or other metal salts. The volume ratio in the dual columns is about three volumes of zinc treated chelating Sepharose ® to one volume of untreated chelating Sepharose ®.

The preferred buffer used to equilibrate the columns is a phosphate buffer at pH 7.2–7.5 containing 1.0M sodium chloride.

In step (b) a special two-part wash with first as an equilibration buffer the phosphate buffer at pH 7.2 containing 1.0M sodium chloride then with the sodium phosphate buffer at pH 7.2–7.5 containing 10% glycerol and a low concentration of sodium chloride (150 mM) are charged to the column. The washes remove impurities, including one which is very closely related and difficult to separate. The active IL-4 remains on the column.

The preferred buffer to maintain the pH of the solution of active IL-4 is a phosphate buffer at pH 7.2 containing 1.0M sodium chloride. When the buffered crude active IL-4 solution is run through the columns, the IL-4 is selectively adsorbed on to the gels.

In step (c) the zinc chelating-Sepharose ® and the untreated chelating Sepharose ® gels are equilibrated with a phosphate buffer at pH 6.75 containing 1.0M sodium chloride then the adsorbed active IL-4 is isocratically eluted from the zinc chelating-Sepharose ® through the untreated chelating-Sepharose ® with an acetate buffer at pH 5.0 with 0.5M sodium chloride or alternatively with a neutral pH buffer containing a chelating agent such as 50 mM EDTA(ethylenediaminetetraacetic acid) or an analog of histidine such as 50 mM imidazole, or an amino acid such as 50 mM histidine. Preferred is the acetate buffer. The eluate containing active IL-4 is collected. The fractions with the highest concentrations of active IL-4 based on the conventional SDS-PAGE and protein assays are pooled.

In step (d) the pH of the pooled fractions from step (c) are adjusted to pH 6.75 and diluted with a 20 mM buffer at pH 6.75 so the conductivity becomes 15 mS. The cation exchange gel material in a chromatography column is equilibrated with a 20 mM phosphate buffer at pH 6.75 having 0.12M sodium chloride. A preferred cation exchange is crosslinked agarose substituted with —$CH_2$—$SO_3$— $Na^+$ groups, such as S-Sepharose ® Fast Flow available from Pharmacia. The active IL-4 is gradient eluted with a 20 mM phosphate buffer at pH 6.75 with 0.12–0.6 M NaCl. The fractions with highest concentrations of active IL-4 based on the SDS-PAGE and protein assays are pooled. The conditions for cation exchange chromatorgraphy are selected to insure that the active IL-4 fraction will attach to the cation exchanger matrix. The near neutral pH 6.75 which is relatively high for a cation exchange chromatography and the 15 mS conductivity which is relatively high for ion exchange chromatography results in mild binding conditions where most impurities do not bind to the column, elution is relatively easy and high purity of the active IL-4 solution is obtained, i.e. about 90%–95%.

In step (e) the pooled eluted fractions from step (d) are concentrated on a stirred cell fitted with a membrane which holds all material with greater than 10,000 molecular weight. This includes active IL-4. Since, at this stage of the process the active IL-4 solution is about 90-95% pure, very little except active IL-4 is in the concentrated solution retained on top of the membrane. A preferred membrane is YM-10 manufactured by Amicon Co., U.S.A. The concentration obtained is up to about 20 mg/mL of active IL-4.

In step (f) the pooled, concentrated eluates of active IL-4 from step (e) are charged to a size exclusion gel filtration column which fractionates proteins in the solution according to molecular weight. A typical column which is suitable is a Sephacryl®S-200 HR or S-100HR(Pharmacia) gel filtration column. The Sephacryl®S-200HR(high resolution) and S-100HR are crosslinked copolymers of allyldextran and N,N'-methylene bisacrylamide. Their fractionation range in Daltons is 5,000-250,000 and 1,000-100,000, respectively. Other suitable materials are the Sephadexes® (Pharmacia) which are crosslinked dextran gels. Preferably the solution of active IL-4 is charged to an S-200 HR column previously equilibrated with a 10 mM citrate buffer at pH 4.5. Under the conditions of step (g) the stable IL-4 concentrate can reach up to 20 mg/ml. This increases the capacity and performance of the gel filtration chromatography.

The fractions of eluate containing the highest concentrations of active IL-4 as determined by the SDS-PAGE and protein assay are collected and pooled to result in a 95-99% pure solution of active IL-4.

Although any solubilized biologically active impure recombinant human interleukin-4 can be purified according to the process of this invention, most practically, the process of this invention is applicable to recombinant human active IL-4 expressed by *E. coli* bacteria which secretes active IL-4 into the culture medium.

In its preferred embodiment, the process of this invention provides for extraction and purification of active human IL-4 produced by *E. coli* genetically engineered to produce active human IL-4 and excrete it into solution in the fermentation broth.

The preferred *E. coli* strains used to prepare the active IL-4 purified according to the preferred embodiment of this invention, as indicated supra, are RL 2117/pRGT857-11 and RL7321/pRGT857-11.

Recovery of the active IL-4 from the culture medium is preferably carried out by centrifuging the culture medium to remove cell debris and other relatively large particles. The resulting solution is then subjected to ultrafiltration on a filter such as a YM-10 membrane or Pellicon filter PTGC cassettes(Millipore Corp., Bedford, Mass.)which retains proteins having molecular weight greater than 10,000. The retentate, which is a concentrated crude solution of active IL-4 is diafiltered with 20 mM phosphate buffer at pH 7.2 containing 1.0M NaCl.

The thus treated crude solution of IL-4 is then purified as described above.

An alternate method to obtain a crude broth which can be purified by this invention is to centifuge the culture medium to remove cell debris and other relatively large particles, form a precipitate of the proteins using 0.50M sodium trichloroacetic acid adjusted to pH4.0 with phosphoric acid and then solubilize the proteins with a 20 mM phosphate buffer at pH 7.2 containing 1.0M NaCl to obtain a concentrated solution of active IL-4. The crude solution is then purified as described above.

The buffers utilized in the process of this invention are chosen because they provide the proper conditions of binding, washing and elution to enable the active IL-4 either to adsorb to the chromatography gels or elute selectively therethrough. The preferred buffers are sodium phosphate buffers at a concentration of 20 mM or sodium citrate or sodium acetate buffers at the concentrations and pHs as shown in the examples, as well as the specific amount of sodium chloride indicated. The pH is adjusted with sodium hydroxide or acid. In the two part wash of step (b), the first wash is with a 20 mM sodium phosphate equilibration buffer at pH 7.2 containing 1.0M sodium chloride, and the second wash is with the phosphate buffer containing about 150 mM sodium chloride and 10% glycerol which is required in the second wash buffer.

The concentration of the sodium chloride in the buffers used with the zinc chelating-Sepharose columns is critical to this invention because high salt, preferably 1M sodium chloride, improves the recovery of solubilized active IL-4 from a trichloroacetic acid (TCA) pellet as well as enhances active IL-4 binding to the metal chelating Sepharose. The concentration enables the IL-4 to be more selectivity adsorbed to the zinc chelating Sepharose column than impurities in the fermentation broth.

The following Examples illustrate the preferred embodiments of this invention.

EXAMPLE 1

PREPARATION OF ZINC CHELATING-SEPHAROSE® FAST FLOW

Slurry chelating Sepharose®Fast Flow gel in deionized water. To prepare a 3 liter column, pour the slurry into a chromatography column 500 mm high with a diameter of 180 mm. Allow the liquid in the column to flow or pump it through the bottom of the column.

Place a top flow adaptor on the column and pack/wash the gel with deionized water. Pump the water through the column at a linear velocity of approximately 1 cm/min. Adjust the top flow adaptor to press firmly on top of the resin bed. Pump at least 5 bed volumes of deionized water through the columns at a linear velocity of approximately 1 cm/min.

Pump approximately 5 bed volumes of 0.023M zinc acetate solution through the column at a linear velocity of approximately 1 cm/minute. Pump approximately 10 bed volumes of deionized water through the column at a linear velocity of approximately 1 cm/min.

Continue pumping the phosphate buffer solution through the column at a linear velocity of approximately 1.0 cm/min. until the pH of the effluent is between 7.1-7.3.

EXAMPLE 2

PREPARATION OF CHELATING SEPHAROSE®FAST FLOW (NOT TREATED WITH A METAL SALT)

Slurry Chelating Sepharose®Fast Flow gel in a buffer composed of 20 mM sodium phosphate at pH7.2 with 1.0M NaCl. To prepare a 1 liter column pour the gel into a chromatography column of 140 mm diameter and 500 mm height and elute from the bottom of the column. Equilibrate the gel with approximately 5 bed volumes of a buffer composed of 20 mM sodium phosphate at pH 7.2 with 1.0M NaCl. Pump the buffer through the column at a linear velocity of approximately 1 cm/min. Continue pumping the buffer through the column at the same flow rate until the pH of the effluent is between 7.1 and 7.3.

EXAMPLE 3

PREPARATION OF COLUMNS IN SERIES

After the zinc chelating Sepharose ® Fast Flow and the untreated chelating Sepharose ®columns are prepared according to Examples 1 and 2, connect the columns in series so the flow is first into the zinc chelating column and then into the non-zinc (untreated) chelating column. A bubble trap should not be inserted between the columns.

EXAMPLE 4

PREPARATION OF S-SEPHAROSE ®COLUMN

Slurry S-Sepharose gel cation exchange resin in a buffer composed of 20 mM sodium phosphate, pH 6.75, 0.12M NaCl and 0.001M ethylene diamine tetraacetic acid (EDTA). Pour the gel into a chromatography column, 100 mm diameter, 45 cm height and allow the liquid to flow or pump it through the bottom of the column.

Place a top flow adapter on the column and equilibrate the gel with 5 bed volumes of a buffer composed of 20 mM sodium phosphate, pH 6.75, 0.12M NaCl, 0.001M EDTA, by pumping the buffer through the column at a linear velocity of approximately 1 cm/min. Adjust the top flow adapter to press firmly on top of the resin bed. Then pump at least 5 bed volumes of a buffer composed of 20 mM sodium phosphate, pH 6.75, 0.12M NaCl, 0.001M EDTA through the column at a linear velocity of approximately 1 cm/min and if necessary continue pumping the buffer through the column at the same flow rate until the pH of the effluent is between 6.6 and 6.9.

EXAMPLE 5

PREPARATION OF SEPHACRYL ®S-200HR COLUMN

Pump at least 1 bed volume of a buffer composed of 10 mM sodium citrate, pH 4.5, through the S 200 HR gel in a chromatography column, 50 mm diameter, 100 cm height, at a linear velocity of approximately 0.2 cm/min to equilibrate the column.

EXAMPLE 6

PREPARATION OF BUFFERS (a) 0.02M Sodium Phosphate, pH 7.2, 1.0M Sodium Chloride Mix together in deionized water 2.78 g/L sodium phosphate monobasic monhydrate, 58.44 g/L sodium chloride and sufficient amount of 6.3N sodium hydroxide to adjust the pH to 7.2(±0.1). The batch should be large enough to provide at least 30 liters per liter of the gels in the metal chelating Sepharose ® columns.

(b) 0.02M Sodium Phosphate, pH 7.2, 0.15M Sodium Chloride, 10% Glycerol

Mix together in deionized water 2.78 g/L sodium phosphate monobasic monohydrate and 8.76 g/L sodium chloride. Adjust the pH to 7.2 (±0.1) with 6.3N sodium hydroxide. Add sufficient glycerol to provide 0.1 L/L. Prepare sufficient amount of the buffer to provide at least 6 liters per liter of the gel with which it will be used.

(c) 0.02M Sodium Acetate, pH 5.0, 0.5M Sodium Chloride

Mix together in deionized water 1.15 ml/L of 99.7% acetic acid and 29.2 g/L sodium chloride. Adjust the pH to 5.0 (±0.1) with 6.3N sodium hydroxide. Prepare sufficient amount of the buffer to provide at least 10 liters per liter of the gel with which it will be used.

(d) 0.03M Sodium Phosphate, pH 7.0, 0.003M EDTA

Mix together in deionized water 4.17 gm/L sodium phosphate monobasic monohydrate and 1.14 g/L tetrasodium EDTA. Adjust the pH to 7.0 (±0.1) with 6.3N sodium hydroxide. Prepare sufficient amount of the buffer to provide at least 2 liters pre liter of gel (e) 10 mM Sodium Citrate, pH 4.5

Mix 210 grams (2.1 g/L) citric acid monohydrate with 100 L deionized water until the citric acid monohydrate is dissolved. Adjust the pH of the buffer to 4.5 with 4N hydrochloric acid and 6.3N sodium hydroxide, if needed. This buffer is used for diafiltration and ultrafiltration as well as for gel filtration chromatography.

EXAMPLE 7

PURIFICATION OF ACTIVE RECOMBINANT HUMAN INTERLEUKIN-4

Zinc chelating Sepharose ® chromatography

Concentrate 700 liters of a fermentation broth in which active human recombinant IL-4 is dissolved to 20 liters, then subject the solution to a 25-fold diafiltration against the buffer of Example 6(a). Adjust the pH of the solution to 7.2 (±0.1) with 4N HCl and/or 6.3N sodium chloride. Adjust the conductivity of the solution to 70–90 mS.

Clarify and concentrate the solution by filtration. Wash the filter with the buffer of Example 6(a) to return the volume of the solution to 20 liters.

Pump the solution through the zinc chelating Sepharose ®Fast Flow and untreated Sepharose ® Fast Flow columns at a linear velocity of approximately 0.5 cm/min. Collect the flow-through in one fraction.

The columns must be washed twice, first with approximately 10 bed volumes of the buffer prepared in Example 6(a) at a linear velocity of approximately 0.5 cm/min and collect the wash in no more than 5 fractions, then with approximately 5 bed volumes of the buffer made in Example 6(b) at a linear velocity of approximately 0.5 cm/min and collect the wash in 1 fraction.

Elute the active IL-4 from the column with approximately 8 bed volumes of the buffer made in Example 6(c) at a linear velocity of approximately 0.25 cm/min. Collect fractions with a volume of approximately 0.2 bed volumes in separate containers containing as a diluent 0.5 ml per ml to be collected of the buffer made in Example 6(d).

Test each sample for active IL-4 with SDS-PAGE and protein assays.

The purity of the active IL-4 solution treated according to this Example 7 is about 20%–40%. The yield of active IL-4 based on the amount in the crude fermentation broth is 90%.

EXAMPLE 8

PREPARATION OF BUFFERS FOR S-SEPHAROSE® CHROMATOGRAPHY (a) 20 mM Sodium Phosphate, pH 6.75, 0.12M Sodium Chloride, 0.001M EDTA Charge 2.78 g/L sodium phosphate monobasic monohydrate, 7.03 g/L sodium chloride, 0.38 g/L tetra sodium EDTA and 1 L/L of deionized water into an appropriate container and agitate until dissolved.

Adjust the pH of the buffer solution to 6.75 ($\pm 0.1$) with 6.3N sodium hydroxide.

(b) 20 mM Sodium Phosphate, pH 6.75 0.55M Sodium Chloride, 0.001M EDTA

Charge 2.78 g/L. sodium phosphate monobasic monohydrate, 32.14 g/L sodium chloride, 0.38 g/L tetra sodium EDTA and deionized water into an appropriate container and agitate until dissolved. Adjust the pH of the buffer solution to 6.75 ($\pm 0.1$) with 6.3N sodium hydroxide.

(c) 20 mM Sodium Phosphate, pH 6.75, 0.001M EDTA

Charge into a container sufficiently large to hold 2.78 g/L sodium phosphate monobasic monohydrate, 0.38 g/L tetra sodium EDTA and deionized water. Agitate until dissolved and adjust the pH of the buffer to 6.75 ($\pm 0.1$) with 6.3N Na OH as required.

EXAMPLE 9

GRADIENT ELUTION OF PURIFIED ACTIVE INTERLEUKIN-4 SOLUTION ON CATION EXCHANGE COLUMN

Adjust the pH of the active IL-4 solution made according to Example 7 to 6.75 ($\pm 0.1$) with either 4NHCl or 6.3N NaOH as required.

Filter through a 0.45 micron filter. Wash the filter with approximately 1 liter of the buffer prepared in Example 8(c).

Adjust the conductivity of the resulting solution to 15 ($\pm 0.5$ mS) with the buffer solution prepared in Example 8(c)

Pump the solution through an S-Sepharose® column as prepared in Example 4 at a linear velocity of approximately 1 cm/min or less. Collect the effluent solution in one fraction.

Wash the column with approximately 5 bed volumes of the buffer solution prepared in Example 8(a) at a linear velocity of approximately 1.0 cm/min or less.

Collect the wash in 1 fraction. Elute the column using a gradient of approximately 4.5 mS per bed volume and a linear flow rate of approximately 0.2 cm/min.

The low salt buffer used in the gradient is that made in Example 8(a), at 5 bed volume and the high salt buffer used in the gradient is that made in Example 8(b), at 5 bed volume.

Collect 5 large fractions, each with a volume of approximately 0.8 bed volumes.

Collect the remaining fractions (about 40-50) in volumes of 0.1 bed volumes.

Test the fractions for active IL-4 by the SDS-PAGE and protein assays.

Pool the active IL-4 fractions. The yield of active IL-4 based on the amount of active IL-4 in the zinc chelating chelating pooled eluates is 90%.

The purity of the active IL-4 solution is about 90% to 95%.

EXAMPLE 10

ULTRAFILTRATION AND CONCENTRATION

Concentrate the pooled fractions from Example 9 using an Amicon stirred chamber fitted with a YM 10 membrane by placing the pooled fractions from Example 9 containing active human IL-4 in a container and concentrating the volume to approximately 0.1 the original volume by ultrafiltration on a YM-10 membrane. Dilute the concentrated retentate with 4 volumes of the buffer prepared in Example 6(e) and concentrate it to approximately 0.2 volumes by ultrafiltration on a YM-10 membrane.

The concentration step can be repeated to achieve approximately 0.1 the volume of the initial pooled fractions. Transfer the concentrate to an appropriate container and hold at cold room temperature or store frozen at $-20°$ C.

EXAMPLE 11

GEL FILTRATION (SIZE EXCLUSION)

Clarify the solution made in Example 10 by centrifugation on a laboratory centrifuge at 4500 rpm for 30 minutes at 2° C.-6° C. Measure the $\text{Å}_{280}$ and dilute the solution with the buffer prepared in Example 6(e) so there are 15 $\text{Å}_{280}$/ml.

Pump the resulting solution onto a Sephacryl® S-200 HR column at a linear velocity of approximately 0.1 cm/min. Continue pumping the buffer of Example 6(e) through the column at a flow rate of approximately 0.1 cm/min. Collect five fractions having a total volume of 0.4 to 0.55 bed volume, then collect 50 fractions of approximately 0.01 bed volume.

Select the fractions with the active IL-4 as determined by SDS-PAGE and protein assay. Pool the active IL-4 fractions and filter through a 0.2 micron sterile filter. Recover the filtrates which are 95% to 99% pure active IL-4 solutions. The overall yield based on the active IL-4 in the fermentation broth is 70-80%.

The purity of the recovered active IL-4 is 95-99% as evidenced by the SDS-PAGE assay.

All the assays used to determine the active fractions of interleukin-4 are conventional. The assays required for selecting active fractions from the eluates are the UV absorbance at 280 nm measurement. For purified IL-4, 1.0 $\text{Å}_{280}$ Optical Density Unit (OD) is equivalent to 1.6 mg by amino acid composition analysis and to 2.0 mg by Lowry's Method.

SDS-PAGE assay is also required for selecting active fractions. This method is discussed in Laemmli, U.K., Nature, 227:680 (1970).

Lowry's Method is described in Lowry et al., J. Biol. Chem. 193, 265-275 (1951).

We claim:

1. A process for purifying a crude solution of active recombinant human interleukin-4, comprising
    (a) charging said crude solution of IL-4 buffered at a neutral to slightly alkaline pH and containing about 0.5-1.5M sodium chloride to a metal chelating agarose gel chromatography column to selectively bind the active recombinant human interleukin-4 to the column;
    (b) washing said column twice, first with an equilibration buffer containing 1.0M sodium chloride and then with a buffer containing 10% glycerol and 0.15M sodium chloride;

(c) eluting the bound active recombinant human interleukin-4 from the column with an eluting buffer at about pH 4.5 to 5.5;

(d) charging the active human IL-4 solution from (c) in a buffer to chromatography on a cation exchanger and gradient eluting a buffered solution of the active human IL-4 from the column;

(e) concentrating the eluate from (d) on a stirred cell membrane that allows matter of less than 10,000 molecular weight to pass;

(f) subjecting the concentrate from (e) to size exclusion chromatography; and (g) recovering the purified solution of active recombinant human interleukin-4.

2. The process of claim 1 wherein in step (a) the buffer is a phosphate buffer of pH 7.5 and the sodium chloride concentration is 1M.

3. The process of claim 2 wherein the metal chelating gel column is a zinc chelating agarose gel.

4. The process of claim 1 wherein in step (b) the buffer is a 0.02 mM sodium phosphate at pH 7.2 also having 150 mM sodium chloride therein.

5. The process of claim 1 wherein in step (c) the pH of the eluting buffer is 5.0.

6. The process of claim 5 wherein in step (c) the buffer is a 0.02 mM sodium acetate buffer with 0.5M sodium chloride.

7. The process of claim 1 wherein in step (d) the charging buffer is a 20 mM phosphate buffer at pH 6.75 with 0.12M sodium chloride.

8. The process of claim 7 wherein the eluting buffer is a 20 mM phosphate buffer at pH 6.75 with about 0.12–0.55M sodium chloride.

9. The process of claim 1 wherein the concentration of step(e) is accomplished by diafiltration against 10 mM sodium citrate buffer at pH 4.5 to a concentration of up to 20 mg/mL.

10. The process of claim 1 wherein in step (f) the size exclusion chromatography is by gel chromatography.

11. A process for purifying an active human interleukin-4 from a crude fermentation broth of a secreted *E. coli* mutant comprising:

(a) centrifuging the crude solution to remove large particle impurities;

(b) subjecting the centrifuged crude solution to diafiltration to concentrate said crude solution;

(c) treating the concentrated crude solution by the process of claim 1.

* * * * *